(12) United States Patent
Grover et al.

(10) Patent No.: US 10,959,788 B2
(45) Date of Patent: Mar. 30, 2021

(54) OFFSET INSTRUMENT DRIVE UNIT

(71) Applicant: Covidien LP, Mansfield, MA (US)

(72) Inventors: Simon Grover, Cambridge (GB); Daniel Fuller, Haverhill (GB); Charles Kilby, Cambridgeshire (GB)

(73) Assignee: Covidien LP, Mansfield, MA (US)

( * ) Notice: Subject to any disclaimer, the term of this patent is extended or adjusted under 35 U.S.C. 154(b) by 333 days.

(21) Appl. No.: 15/578,797

(22) PCT Filed: May 27, 2016

(86) PCT No.: PCT/US2016/034509
§ 371 (c)(1),
(2) Date: Dec. 1, 2017

(87) PCT Pub. No.: WO2016/196238
PCT Pub. Date: Dec. 8, 2016

(65) Prior Publication Data
US 2018/0153628 A1 Jun. 7, 2018

Related U.S. Application Data

(60) Provisional application No. 62/170,298, filed on Jun. 3, 2015.

(51) Int. Cl.
*A61B 34/30* (2016.01)
*A61B 34/35* (2016.01)
(Continued)

(52) U.S. Cl.
CPC .......... *A61B 34/30* (2016.02); *A61B 17/068* (2013.01); *A61B 34/00* (2016.02); *A61B 34/35* (2016.02);
(Continued)

(58) Field of Classification Search
CPC .......................................... A61B 2017/00477
(Continued)

(56) References Cited

U.S. PATENT DOCUMENTS 4,988,273 A * 1/1991 Faig .................... B29C 45/5008
425/145
5,146,145 A * 9/1992 Wood .................... H02K 21/16
318/400.04
(Continued)

FOREIGN PATENT DOCUMENTS

CN 102119872 A 7/2011
CN 104334111 A 2/2015
(Continued)

OTHER PUBLICATIONS

Extended European Search Report issued in Application No. 16804085.5, dated Jan. 17, 2019 (10 pages).
(Continued)

*Primary Examiner* — Eduardo Colon Santana
*Assistant Examiner* — Devon A Joseph
(74) *Attorney, Agent, or Firm* — Carter DeLuca & Farrell LLP

(57) ABSTRACT

A surgical system for selective connection to a robotic arm includes an instrument drive unit and a surgical instrument detachably coupled to the instrument drive unit. The instrument drive unit includes a first actuator, a linkage member having opposing first and second portions, and a drive member. The first portion of the linkage member is operatively coupled to the first actuator such that actuation of the first actuator moves the first portion in a first direction and the second portion in a second direction opposite of the first direction. The drive member is operatively coupled to the second portion of the linkage member. The surgical instrument includes a driven member operatively associated with (Continued)

the drive member of the instrument drive unit and an end effector operatively coupled with the driven member, wherein translation of the driven member effects a first function of the end effector.

25 Claims, 6 Drawing Sheets

(51) Int. Cl.
*A61B 34/00* (2016.01)
*A61B 17/068* (2006.01)
*A61B 17/00* (2006.01)

(52) U.S. Cl.
CPC .............. *A61B 34/70* (2016.02); *A61B 34/71* (2016.02); *A61B 2017/00473* (2013.01); *A61B 2017/00477* (2013.01)

(58) Field of Classification Search
USPC ........................................................ 318/568
See application file for complete search history.

(56) References Cited

U.S. PATENT DOCUMENTS

| | | | | |
|---|---|---|---|---|
| 5,817,084 | A * | 10/1998 | Jensen | B25J 9/1065 606/1 |
| 6,436,107 | B1 * | 8/2002 | Wang | A61B 1/00149 318/568.11 |
| 7,886,743 | B2 | 2/2011 | Cooper et al. | |
| 7,963,913 | B2 | 6/2011 | Devengenzo et al. | |
| 8,337,515 | B2 | 12/2012 | Viola et al. | |
| 8,640,788 | B2 * | 2/2014 | Dachs, II | A61B 34/30 173/164 |
| 8,828,023 | B2 | 9/2014 | Neff et al. | |
| 9,402,555 | B2 * | 8/2016 | Kirschenman | A61M 25/0113 |
| 9,737,371 | B2 * | 8/2017 | Romo | A61B 34/32 |
| 9,987,094 | B2 * | 6/2018 | Allen | H02P 9/00 |
| 10,016,900 | B1 * | 7/2018 | Meyer | A61B 34/30 |
| 10,130,427 | B2 * | 11/2018 | Tanner | A61B 34/30 |
| 10,470,830 | B2 * | 11/2019 | Hill | A61B 90/37 |
| 2006/0084945 | A1 | 4/2006 | Moll et al. | |
| 2008/0119870 | A1 | 5/2008 | Williams | |
| 2010/0204646 | A1 | 8/2010 | Plicchi et al. | |
| 2011/0118754 | A1 * | 5/2011 | Dachs, II | A61B 34/30 606/130 |
| 2011/0277775 | A1 | 11/2011 | Holop et al. | |
| 2012/0116416 | A1 | 5/2012 | Neff et al. | |
| 2013/0172713 | A1 * | 7/2013 | Kirschenman | A61B 5/042 600/373 |
| 2013/0325034 | A1 | 12/2013 | Schena et al. | |
| 2014/0005653 | A1 | 1/2014 | Shelton, IV et al. | |
| 2014/0222207 | A1 * | 8/2014 | Bowling | B25J 9/1633 700/261 |
| 2014/0276761 | A1 | 9/2014 | Parihar et al. | |
| 2014/0303434 | A1 | 10/2014 | Farritor et al. | |
| 2015/0142013 | A1 * | 5/2015 | Tanner | A61B 6/4423 606/130 |
| 2015/0297199 | A1 | 10/2015 | Nicholas et al. | |
| 2016/0184032 | A1 * | 6/2016 | Romo | B25J 9/1694 606/130 |
| 2016/0346049 | A1 * | 12/2016 | Allen | A61B 90/06 |
| 2017/0007336 | A1 * | 1/2017 | Tsuboi | B25J 9/06 |
| 2017/0007342 | A1 * | 1/2017 | Kasai | A61B 90/06 |
| 2018/0110576 | A1 * | 4/2018 | Kopp | A61B 34/35 |

FOREIGN PATENT DOCUMENTS

| | | |
|---|---|---|
| CN | 104349741 A | 2/2015 |
| CN | 107735044 A | 2/2018 |
| EP | 0705571 A1 | 4/1996 |
| JP | H07194609 A | 8/1995 |
| JP | 2003024336 A | 1/2003 |
| JP | 2008036793 A | 2/2008 |
| JP | 2013153295 A * | 8/2013 |
| JP | 2016514009 A | 5/2016 |
| WO | 2011-060318 A1 | 5/2011 |
| WO | 2013101269 A1 | 7/2013 |
| WO | 2014-163787 A1 | 10/2014 |
| WO | 2015012023 A1 | 1/2015 |
| WO | 2015-088647 A1 | 6/2015 |
| WO | 2016183054 A1 | 11/2016 |

OTHER PUBLICATIONS

Chinese Office Action issued in Chinese Patent Application No. 201680031902.9, dated Dec. 3, 2019.
Japanese Office Action issued in Japanese Patent Application No. 2017-560974, dated Feb. 25, 2020.

* cited by examiner

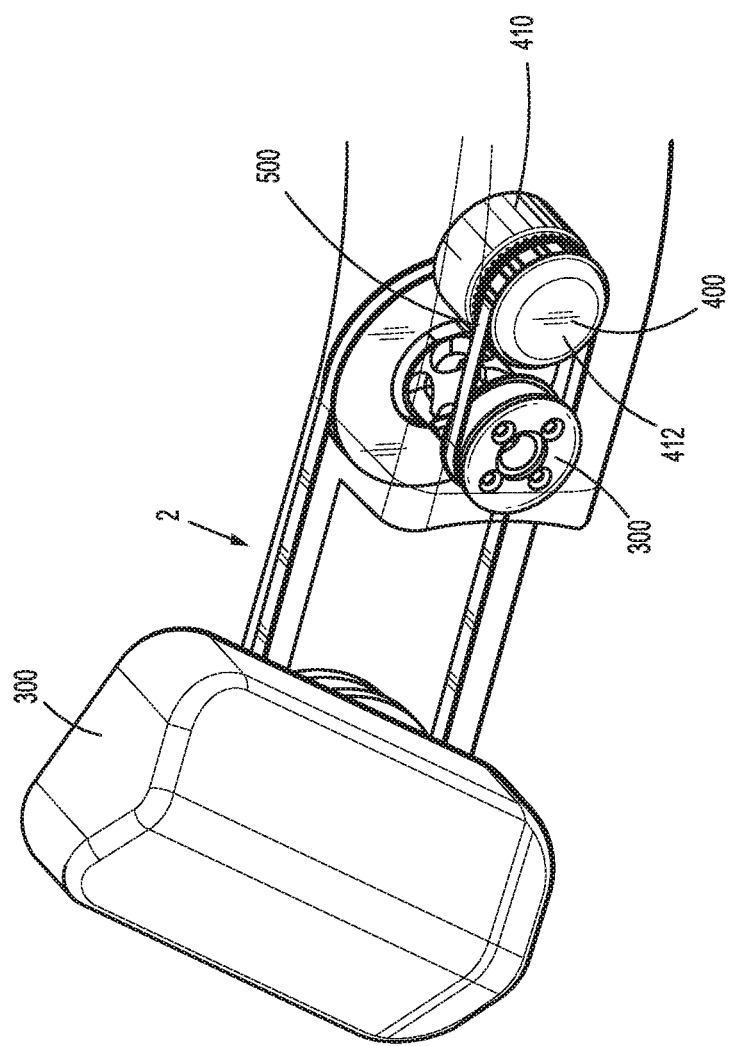

OFFSET INSTRUMENT DRIVE UNIT

CROSS-REFERENCE TO RELATED APPLICATIONS

The present application claims priority to, and the benefit of, U.S. Provisional Patent Application Ser. No. 62/170,298, filed on Jun. 3, 2015, the contents of which are hereby incorporated by reference in its entirety.

BACKGROUND

Robotic surgical systems used in minimally invasive medical procedures include a console or cart supporting a robot arm and a surgical instrument having an end effector that may include, for example, forceps, a stapler, or a grasping tool. The robot arm provides mechanical power to the surgical instrument for its operation and movement. Each robot arm may include an instrument drive unit that is operatively connected to the surgical instrument.

Prior to or during use of the robotic system, surgical instruments are selected and connected to the instrument drive units of each robot arm. For proper installation to be completed, certain connecting features of the surgical instrument must be matingly engaged to corresponding connecting features of the instrument drive unit. Once these features are matingly engaged, the instrument drive unit can drive the actuation of the surgical instrument. However, connection and removal of surgical instruments to instrument drive units can be difficult.

Accordingly, new robotic devices, systems, and methods that are reliable and that enable easy and efficient attachment and removal of surgical instruments would be desirable.

SUMMARY

The present disclosure describes robotic devices, systems, and methods that demonstrate a practical approach to meeting the performance requirements and overcoming the usability challenges associated with instrument attachment and removal. In general, the present disclosure describes robotic surgical systems that include an instrument drive unit and a surgical instrument support coupled to the instrument drive unit. The surgical instrument includes an end effector controllable to perform surgery in response to telemanipulation of actuators in the instrument drive unit.

In accordance with an embodiment of the present disclosure, there is provided a surgical system for selective connection to a robotic arm. The surgical system includes an instrument drive unit and a surgical instrument detachably coupled to the instrument drive unit. The instrument drive unit includes a first actuator, a linkage member having opposing first and second portions, and a drive member operatively coupled to the second portion of the linkage member. The first portion of the linkage member is operatively coupled to the first actuator such that actuation of the first actuator moves the first portion in a first direction and the second portion in a second direction opposite of the first direction. The surgical instrument includes a driven member operatively associated with the drive member of the instrument drive unit and an end effector operatively coupled with the driven member, wherein translation of the driven member effects a first function of the end effector.

In an embodiment, the linkage member may be pivotally supported about a pivot disposed between the first and second portions.

In another embodiment, the instrument drive unit may include a first elongate member having a first sleeve translatably mounted on the first elongate member. The first sleeve may be operatively associated with the first portion of the linkage member, such that rotation of the first elongate member pivots the linkage member about the pivot. In addition, the first sleeve may be threadably mounted on the first elongate member.

In another embodiment, the first sleeve may have a first camming pin and the first portion of the linkage member may define a first slot configured to slidably receive the first camming pin of the first sleeve, whereby translation of the first sleeve causes relative movement of the first camming pin within the first slot. Further, the first elongate member may include a pulley operatively coupled to the first actuator, wherein actuation of the first actuator causes rotation of the first elongate member.

In yet another embodiment, the instrument drive unit may further include a second elongate member having a second sleeve translatably mounted on the second elongate member. The second sleeve may be operatively associated with the second portion of the linkage member. In particular, the second sleeve may have a second camming pin, and the second portion of the linkage member may define a second slot configured to slidably receive the second camming pin of the second sleeve, whereby translation of the second sleeve causes relative movement of the second pin within the second slot.

In yet another embodiment, the surgical instrument may further include a first cable having a first end coupled to the driven member of the surgical instrument and a second end operatively associated with the end effector.

In an embodiment, the first actuator of the instrument drive unit may be controlled by telemanipulation.

In still another embodiment, the instrument drive unit may further include a second actuator and a rotatable member operatively coupled with the second actuator, and the surgical instrument may further include a gear member configured to operatively engage the rotatable member of the instrument drive unit and the end effector for concomitant rotation with the end effector.

In an embodiment, the first and second actuators may be independently actuatable.

In another embodiment, the instrument drive unit may be offset from a longitudinal axis defined by the robotic arm.

In yet another embodiment, the surgical instrument may include an elongate member extending distally from the driven assembly. The elongate member may support the end effector at a distal end of the elongate member.

In accordance with another aspect of the present disclosure, there is provided a robotic surgical assembly including a robotic arm having a mount, an instrument drive unit mounted on the mount of the robotic arm, and a surgical instrument detachably coupled to the instrument drive unit. The instrument drive unit includes a plurality of actuators, a plurality of linkage members, and a plurality of drive members. Each linkage member has opposing first and second portions. The first portion is operatively coupled to respective one of the plurality of actuators such that actuation of the respective one of the plurality of actuators moves the first portion in a first direction and the second portion in a second direction opposite of the first direction. Each one of the plurality of drive members is operatively coupled to the second portion of respective one of the plurality of linkage members. The surgical instrument includes a plurality of driven members and an end effector operatively coupled with the plurality of driven members. Each of the plurality of driven members is operatively associated with respective one of the plurality of drive members of the instrument drive unit, wherein translation of at least one of the plurality of driven members effects a first function of the end effector.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 8 is a perspective view of a torque sensor assembly for use with the robotic arm of FIG. 2.

DETAILED DESCRIPTION

Figure 1:
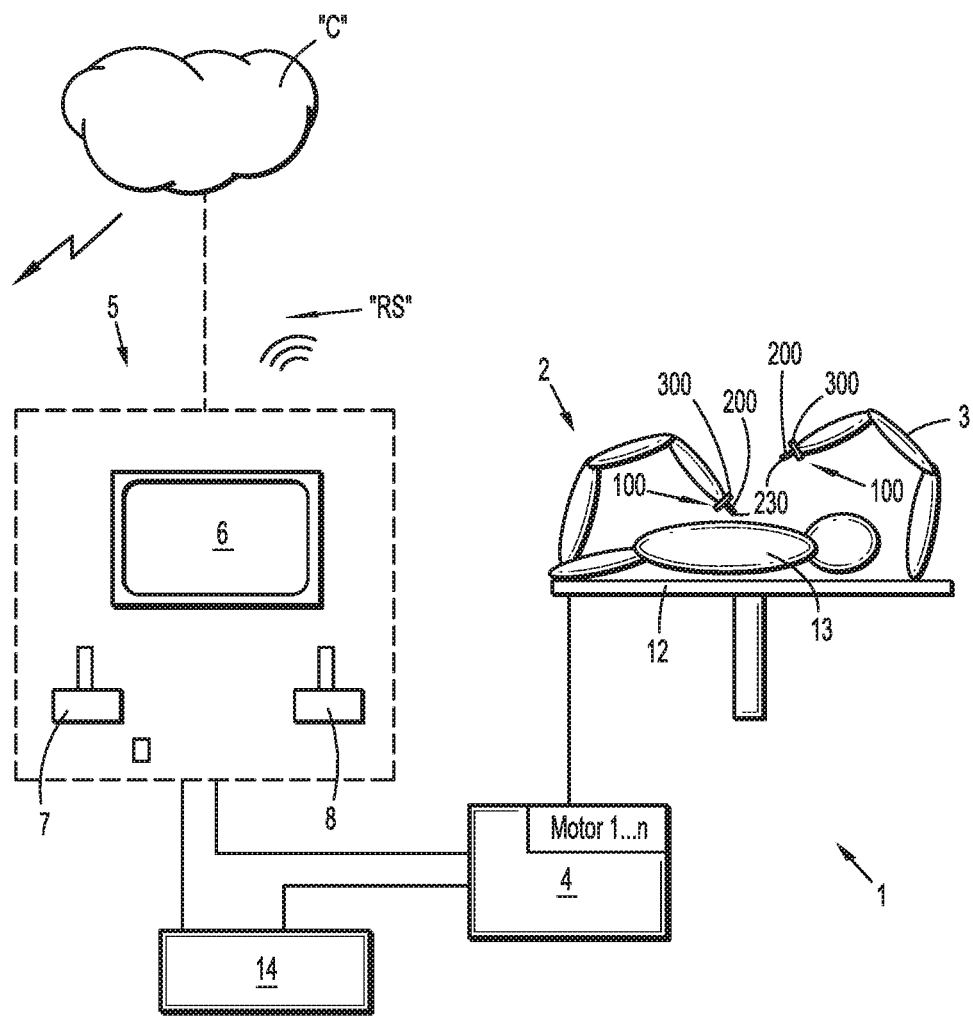
FIG. 1 is a schematic illustration of a robotic surgical system in accordance with the present disclosure.

Embodiments of the present disclosure are described in detail with reference to the drawings, in which like reference numerals designate identical or corresponding elements in each of the several views. As used herein, the term "distal" refers to that portion of a device that is farther from the user, while the term "proximal" refers to that portion of a device that is closer to the user.

With reference to FIG. 1, there is provided a robotic surgical system 1 including a plurality of robotic arms 2, 3; a control device 4; and an operating console 5 coupled with control device 4. Operating console 5 includes a display device 6 and manual input devices 7, 8, by means of which a person (not shown), for example, a surgeon, is able to telemanipulate robotic arms 2, 3.

Each of the plurality of robotic arms 2, 3 includes a plurality of members, which are connected through joints. Robotic surgical system 1 also includes a surgical assembly 100 connected to a distal end of each of robotic arms 2, 3. Surgical assembly 100 includes an instrument drive unit 300 and a surgical instrument 200 detachably coupled to instrument drive unit 300. Surgical instrument 200 includes an end effector 230.

Robotic arms 2, 3 may be driven by electric drives (not shown) that are connected to control device 4. Control device 4 (e.g., a computer) is set up to activate the drives, in particular by means of a computer program, in such a way that surgical assembly 100 of respective robotic arms 2, 3 executes a desired movement according to a movement defined by means of manual input devices 7, 8. Control device 4 may also be set up in such a way that it regulates movement of robotic arms 2, 3 and/or of the drives.

With continued reference to FIG. 1, robotic surgical system 1 is configured for use on a patient 13 lying on a patient table 12 for a minimally invasive procedure by means of end effector 230. Robotic surgical system 1 may include more than two robotic arms 2, 3. The additional robotic arms may also be connected to control device 4 and may be telemanipulatable by means of operating console 5. One or more additional surgical assemblies 100 and/or surgical instruments 200 may also be attached to the additional robotic arm.

Control device 4 may control a plurality of motors (Motor 1 . . . n) with each motor configured to drive a pushing or a pulling of one or more cables coupled to end effector 230 of surgical instrument 200. While cables are shown and described, it is contemplated that cables can be replaced with rods or the like. In use, as these cables are pushed and/or pulled, the cables effect operation and/or movement of end effector 230 of surgical instrument 200. It is contemplated that control device 4 coordinates the activation of the various motors (Motor 1 . . . n) to coordinate a pushing or a pulling motion of one or more cables in order to coordinate an operation and/or movement of one or more end effectors 230. In embodiments, each motor can be configured to actuate a drive rod or a lever arm to effect operation and/or movement of end effectors 230 in addition to, or instead of, one or more cables.

Control device 4 can include any suitable logic control circuit adapted to perform calculations and/or operate according to a set of instructions. Control device 4 can be configured to communicate with a remote system "RS," either via a wireless (e.g., Wi-Fi™, Bluetooth®, LTE™, etc.) and/or wired connection. Remote system "RS" can include data, instructions and/or information related to the various components, algorithms, and/or operations of robotic surgical system 1. Remote system "RS" can include any suitable electronic service, database, platform, cloud "C", or the like. Control device 4 may include a central processing unit operably connected to memory. The memory may include transitory type memory (e.g., RAM) and/or non-transitory type memory (e.g., flash media, disk media, etc.). In some embodiments, the memory is part of, and/or operably coupled to, remote system "RS."

Control device 4 can include a plurality of inputs and outputs for interfacing with the components of robotic surgical system 1, such as through a driver circuit. Control device 4 can be configured to receive input signals and/or generate output signals to control one or more of the various components (e.g., one or more motors) of robotic surgical system 1. The output signals can include, and/or can be based upon, algorithmic instructions which may be pre-programmed and/or input by a user. Control device 4 can be configured to accept a plurality of user inputs from a user interface (e.g., switches, buttons, touch screen, etc. of operating console 5) which may be coupled to remote system "RS."

A database 14 can be directly and/or indirectly coupled to control device 4. Database 14 can be configured to store pre-operative data from living being(s) and/or anatomical atlas(es). Database 14 can include memory which can be part of, and/or or operatively coupled to, remote system "RS." Reference may be made to U.S. Patent Publication No. 2012/0116416, filed on Nov. 3, 2011, entitled "Medical Workstation," the entire content of which is incorporated herein by reference, for a detailed discussion of the construction and operation of robotic surgical system 1.

Figure 2:
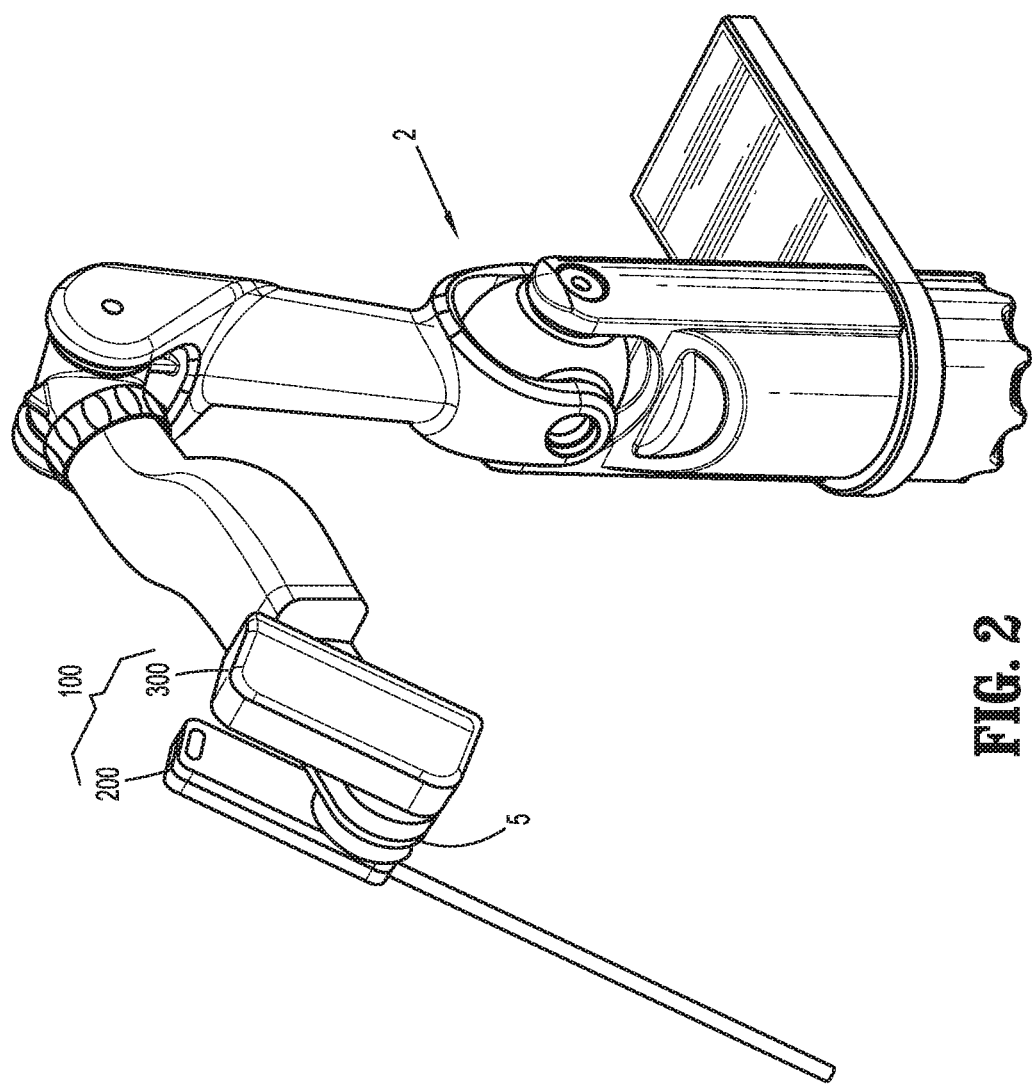
FIG. 2 is a perspective view of a robotic arm having a surgical assembly mounted thereon.
Figure 3:
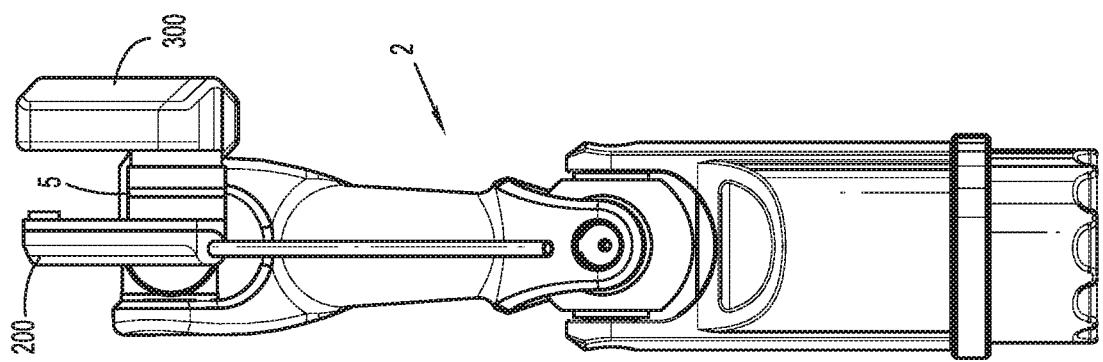
FIG. 3 is a front view of the robotic arm and the surgical assembly of FIG. 2.

Turning now to FIGS. 2 and 3, surgical assembly 100 includes instrument drive unit 300 coupled to a mount 5

Figure 4:
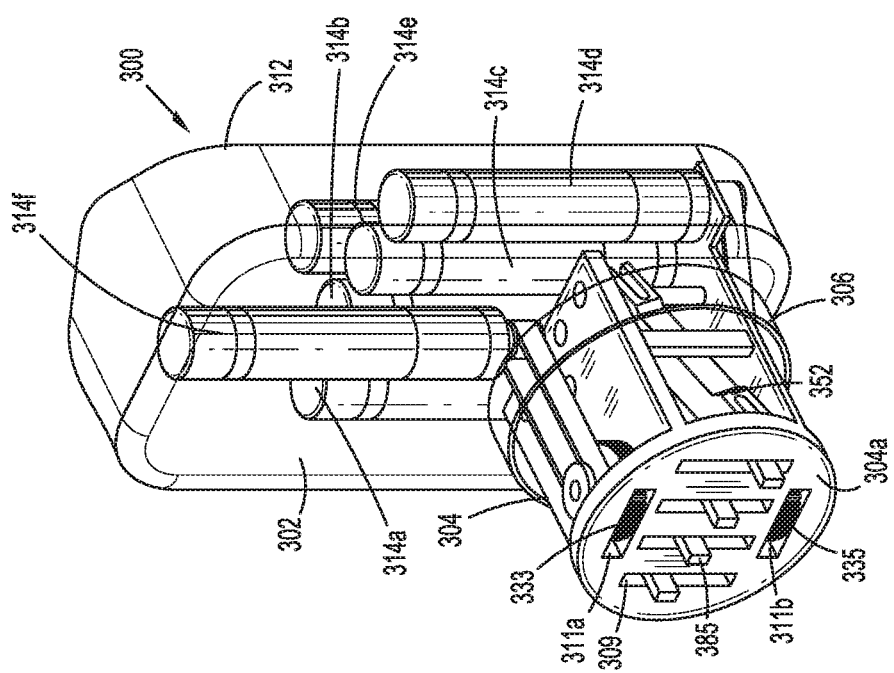
FIG. 4 is a perspective view of an instrument drive unit of the surgical assembly of FIG. 2 showing actuators and a drive system in phantom.

(FIG. 3) of robotic arm 2 and surgical instrument 200 releasably coupled to instrument drive unit 300. With reference now to FIG. 4, instrument drive unit 300 includes a body 312 having an actuation housing 302 and an adapter portion 304 extending transversely from actuation housing 302. Actuation housing 302 includes an annular rim 306 configured to securely support at least a portion of adapter portion 304 therein. Adapter portion 304 has a circular cross-section configured to extend through mount 5 of robotic arm 2. Adapter portion 304 includes an engaging surface 304a configured to operatively engage a portion of a contact surface 204 (FIG. 6) of surgical instrument 200.

Figure 5:
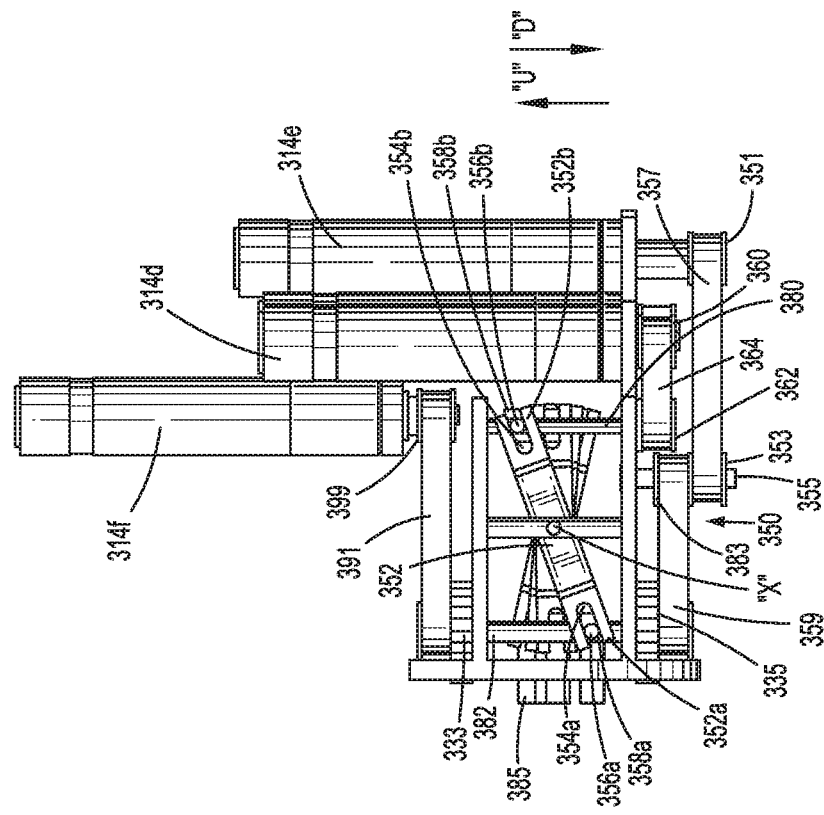
FIG. 5 is a side view of the actuators and the drive system of FIG. 4.

With reference now to FIGS. 4 and 5, actuation housing 302 supports a plurality of actuators or motors 314a-f. Adapter portion 304 includes a drive system 350 having a plurality of pivotably supported linkage members 352, a plurality of threaded members 380 (only one shown in FIG. 5), and a plurality of elongated members or shafts 382 (only one shown in FIG. 5). The plurality of pivotably supported linkage members 352 are configured to pivot about a common pivot "X". Each of the plurality of pivotably supported linkage members 352 includes opposing first and second portions 352a, 352b. Each of the plurality of threaded members 380 includes a sleeve or nut 358b threadably coupled with threaded member 380. Each of the plurality of elongated members 382 includes a sleeve 358a configured to slidably translate along respective elongated member 382.

Each of first and second portions 352a, 352b of linkage members 352 defines a slot 354a, 354b, respectively. Each slot 354a, 354b is configured to slidably receive a camming pin 356a of sleeve 358a and a camming pin 356b of sleeve 358b, respectively. Under such a configuration, rotation of threaded member 380 causes translation of sleeve 358b along respective threaded member 380. Translation of sleeve 358b along threaded member 380 causes relative movement between camming pin 356b and slot 354b and between camming pin 356a and slot 354a such that opposing first and second portions 352a, 352b move in opposite directions, as shown by arrows "D", "U" (FIG. 5), in the manner of a see-saw. Each of the plurality of sleeves 358a is connected to a respective one of a plurality of linear drives 385.

With continued reference to FIGS. 4 and 5, each of actuators or motors 314a-d includes a first pulley 360, and each of the plurality of threaded members 380 includes a second pulley 362. First pulley 360 and second pulley 362 are operatively coupled by a drive belt 364 such that rotation of first pulley 360 imparts rotation to second pulley 362. Rotation of second pulley 362 imparts concomitant rotation to threaded member 380, which in turn, causes translation of sleeve 358b along threaded member 380. Translation of sleeve 358b in, e.g., the direction of arrow "U", causes translation of sleeve 358a in the opposite direction, i.e., in the direction of arrow "D", to drive linear drive 385.

With particular reference back to FIG. 4, engaging surface 304a of adapter portion 304 defines a plurality of slots 309 configured to receive a respective linear drive 385 therein. Each linear drive 385 is slidable within respective slot 309 and extends through respective slot 309 such that each linear drive 385 engages a respective driven member 262a-d (FIG. 7) of surgical instrument 200, as will be described hereinbelow. In addition, engaging surface 304a further defines apertures 311a, 311b configured to receive gears 333, 335, respectively.

With particular reference to FIG. 5, actuator or motor 314e is coupled to a pulley 351 that is operatively coupled to a pulley 353 by a drive belt 357. Pulley 353 is secured to an elongate shaft 355 for concomitant rotation therewith. A pulley 383 is also secured to elongate shaft 355 for concomitant rotation therewith. Pulley 383 is operatively coupled to gear 335 by a second drive belt 359. Under such a configuration, actuation of actuator or motor 314e causes rotation of gear 335. At least a portion of gear 335 extends through aperture 311b (FIG. 4) such that gear 335 engages gear 227c of instrument interface 220 (FIG. 7) on surgical instrument 200, as will be discussed hereinbelow.

In addition, actuator or motor 314f is operatively coupled to pulley 399 that is coupled to gear 333 by a drive belt 391. Under such a configuration, actuation of actuator or motor 314f causes rotation of gear 333. At least a portion of gear 333 extends through aperture 311a (FIG. 4) for engagement with a gear 227b (FIG. 6) of instrument interface 220.

Figure 7:
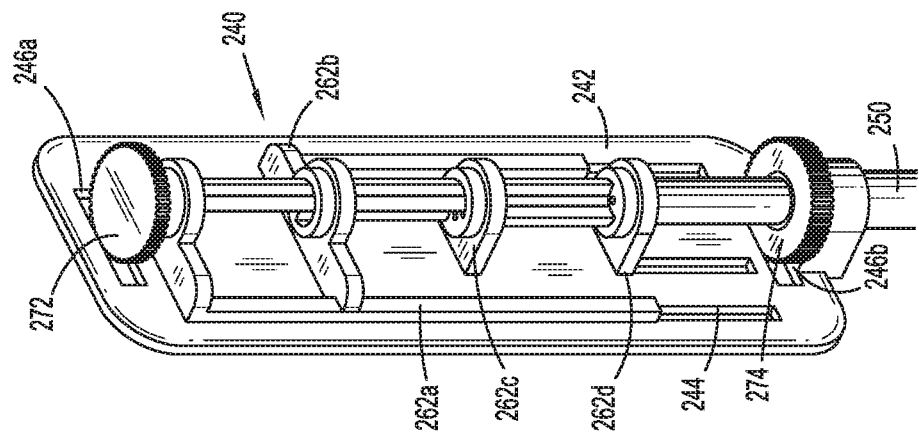
FIG. 7 is a perspective view of the driven assembly of FIG. 6 with a housing portion removed.
Figure 6:
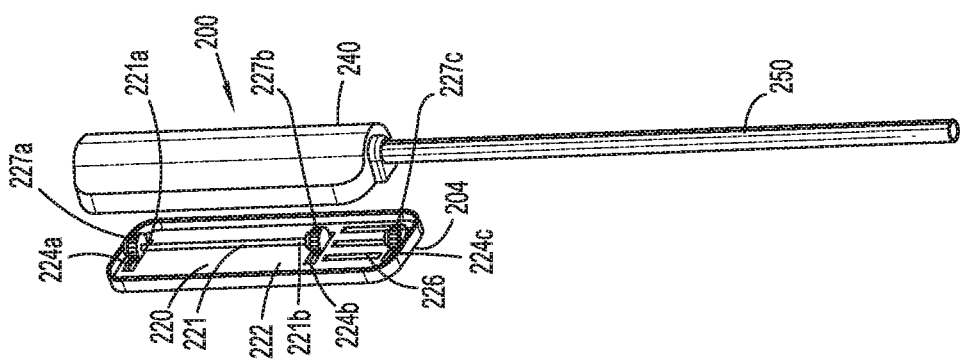
FIG. 6 is a perspective view of a surgical instrument of FIG. 2 showing an instrument interface detached from a driven assembly.

With reference now to FIGS. 6 and 7, a surgical instrument 200 includes an instrument interface 220, a driven assembly 240, and an elongate member 250, and an end effector 230 (FIG. 1) supported at a distal end of elongate member 250. Driven assembly 240 includes a support panel 242 defining a plurality of slots 244 along a length of support panel 242 and apertures 246a, 246b. Driven assembly 240 further includes a plurality of driven members 262a-d. A portion of each of the plurality of driven members 262a-d extends through a respective slot 244 and is translatable therewithin. Driven assembly 240 further includes gears 272, 274. At least a portion of each gear 272, 274 extends through a respective aperture 246a, 246b. Gear 274 is secured with elongate member 250 for concomitant rotation therewith.

With particular reference now to FIG. 6, instrument interface 220 includes a body panel 222 configured to be operatively mounted on driven assembly 240. Body panel 222 defines a plurality of apertures 224a-c and a plurality of slots 226. The plurality of apertures 224a-c are configured to receive at least a portion of a respective gear 227a-c therethrough. Each of the plurality of slots 226 aligns with a respective slot 244 of support panel 242 of driven assembly 240 such that a portion of each of the plurality of driven members 262a-d of driven assembly 240 extends through the respective slot 226 of instrument interface 220. The portion of each of the plurality of driven member 262a-d of driven assembly 240 operatively engages a respective linear drive 385 of instrument actuation drive 300. Under such a configuration, actuation of actuators or motors 314a-d causes translation of respective driven members 262a-d of driven assembly 240.

Each of the plurality of driven members 262a-d is coupled to a cable or rod (not shown) operatively associated with end effector 230 to effect a function of end effector 230. In particular, each cable may be coupled to end effector 230 such that actuation of each cable or combinations thereof performs a function of end effector 230. Longitudinal translation of one or more of cables may impart movement (e.g., rotation, pivoting, articulation, longitudinal/lateral translation, etc.) on end effector 230, or portions thereof. For instance, U.S. patent application Ser. No. 14/257,063, filed Apr. 21, 2014, and entitled "Adapter Assembly with Gimbal for Interconnecting Electromechanical Surgical devices and Surgical Loading Units, and Surgical Systems Thereof," the entire contents of which are hereby incorporated by reference, describes surgical stapling devices with end effectors that support distally advanceable sleds operatively coupled to a rotatable lead screw to fire surgical staples. Elongate member 250 is dimensioned to receive the plurality of cables and to enable each of the plurality of cables to linearly translate therethrough.

With continued reference to FIGS. 6 and 7, gear 227c of instrument interface 220 is configured to be aligned with and engage gear 274 of driven assembly 240. Gear 335 of instrument actuation device 300 is configured to engage gear 227c of instrument interface 220 such that actuation of actuator or motor 314e rotates gear 335 (FIG. 5), which in turn, rotates gear 227c of instrument interface 220 and gear 274 of driven assembly 240. Rotation of gear 274 of driven assembly 240 causes concomitant rotation of elongate member 250, which imparts rotation to end effector 230.

With particular reference to FIG. 6, instrument interface 220 further includes a rotatable shaft 221 having first and second ends 221a, 221b. First and second ends 221a, 221b include gears 227a, 227b respectively, for concomitant rotation with rotatable shaft 221. A portion of gear 227b extends through aperture 224b defined in body panel 222 and engages gear 333 of instrument drive unit 300. Under such a configuration, actuation of actuator or motor 314f causes rotation of gear 333, which in turn, imparts rotation to gear 227b. Rotation of gear 227b imparts concomitant rotation to gear 227a. Gear 227a of instrument interface 220 engages gear 272 of driven assembly 240. Gear 272 may be operatively coupled with end effector 230 to effect a function of end effector 230.

With reference now to FIG. 8, robotic arm 2 supports a rotatable torque sensor 300 and a motor assembly 400 that are coupled together by a drive belt 500. Torque sensor 300 supports electrical components (e.g., resistors, wires, etc.) configured to communicate with control device 4 to provide torque feedback data, for example. Motor assembly 400 includes a motor 410 and a harmonic gear box 412 that cooperate to impart rotation on torque sensor 300 via drive belt 500 to effect rotation of instrument drive unit 300.

In operation, with reference to FIGS. 4-7, instrument drive unit 300 is mounted on mount 5 of robotic arm 2, and surgical instrument 200 is detachably coupled to instrument drive unit 300. Each linear drive 385 of instrument drive unit 300 engages respective driven member 262a-d of driven assembly 240 of surgical instrument 200. Further, gear 333 of instrument drive member 300 engages gear 227b of instrument interface 220 of surgical instrument 200. In addition, gear 335 of instrument drive unit 300 engages gear 227c of instrument interface 220 of surgical instrument 200. With surgical instrument 200 operatively coupled to instrument drive unit 300, one or more of the plurality of actuators or motors 314a-d are activated to rotate one or more of threaded member 380, which in turn, causes translation of one or more linear drives 385 of instrument drive unit 300. Actuation of one or more linear drives 385 causes translation of driven members 262a-d within slot 244 of support panel 242 of surgical instrument 200. Translation of driven members 262a-d translates the respective cable. Translation of cables, or combinations thereof, imparts movement (e.g., rotation, pivoting, articulation, longitudinal/lateral translation, etc.) on end effector 230, or portions thereof.

In addition, actuation of actuator or motor 314e causes rotation of gear 335, which in turn, imparts rotation to gear 227c of instrument interface 220. Rotation of gear 227c causes rotation of gear 274, which in turn, imparts concomitant rotation to elongate member 250. Rotation of elongate member 250 causes concomitant rotation of end effector 230. In addition, actuation of actuator or motor 314f causes rotation of gear 333 of instrument drive unit 300, which engages gear 227b of instrument interface 220 and causes rotation of gear 227b. Gear 227b imparts concomitant rotation to gear 227a of instrument interface 220. Gear 227a engages gear 272 of driven assembly 240. Under such a configuration, rotation of gear 227a of instrument interface 220 causes rotation of gear 272 of driven assembly 240. Gear 272 may be operatively coupled with end effector 230 to effect additional function of end effector 230.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical system for selective connection to a robotic arm comprising:
   an instrument drive unit including:
      a first actuator;
      first and second elongate members being axially stationary, the first elongate member operatively coupled to the first actuator such that actuation of the first actuator rotates the first elongate member about a first longitudinal axis of the first elongate member;
      a first sleeve disposed about the first elongate member such that rotation of the first elongate member about the first longitudinal axis translates the first sleeve along the length of the first elongate member;
      a linkage member having opposing first and second portions, the first portion operatively coupled to the first sleeve such that actuation of the first actuator moves the first portion in a first direction and the second portion in a second direction opposite of the first direction, the linkage member pivotally supported about a pivot disposed between the first and second portions, the first and second portions pivotable as a single construct such that the first and second portions are axially aligned; and
      a drive member operatively coupled to the second portion of the linkage member; and
   a surgical instrument detachably coupled to the instrument drive unit, the surgical instrument including:
      a driven member operatively associated with the drive member of the instrument drive unit; and
      an end effector operatively coupled with the driven member,
   wherein translation of the driven member effects a first function of the end effector.

2. The surgical system of claim 1, wherein the first sleeve is threadably mounted on the first elongate member.

3. The surgical system of claim 2, wherein the first sleeve has a first camming pin and the first portion of the linkage member defines a first slot configured to slidably receive the first camming pin of the first sleeve, whereby translation of the first sleeve causes relative movement of the first camming pin within the first slot.

4. The surgical system of claim 1, wherein the first elongate member includes a pulley operatively coupled to the first actuator.

5. The surgical system of claim 1, wherein the second elongate member includes a second sleeve translatable along the length of the second elongate member, the second sleeve operatively associated with the second portion of the linkage member.

6. The surgical system of claim 5, wherein the second sleeve has a second camming pin, and the second portion of the linkage member defines a second slot configured to slidably receive the second camming pin of the second sleeve, whereby translation of the second sleeve causes relative movement of the second pin within the second slot.

7. The surgical system of claim 1, wherein the surgical instrument further includes a first cable having a first end coupled to the driven member of the surgical instrument and a second end operatively associated with the end effector.

8. The surgical system of claim 1, wherein the first actuator of the instrument drive unit is controlled by telemanipulation.

9. The surgical system of claim 1, wherein the instrument drive unit further includes a second actuator and a rotatable member operatively coupled with the second actuator, and the surgical instrument further includes a gear member configured to operatively engage the rotatable member of the instrument drive unit and the end effector for concomitant rotation with the end effector.

10. The surgical system of claim 9, wherein the first and second actuators are independently actuatable.

11. The surgical system of claim 1, wherein the instrument drive unit is offset from a longitudinal axis defined by the robotic arm.

12. The surgical system of claim 1, wherein the surgical instrument includes an elongate member extending distally from the driven assembly, the elongate member supporting the end effector at a distal end of the elongate member.

13. A robotic surgical assembly comprising:
a robotic arm having a mount;
an instrument drive unit mounted on the mount of the robotic arm, the instrument drive unit including:
  a plurality of actuators;
  a plurality of first elongate members, each first elongate member of the plurality of first elongate members including a first sleeve such that rotation of the first elongate member about a longitudinal axis thereof causes axial displacement of the first sleeve on the first elongate member;
  a plurality of second elongate members, each second elongate member of the plurality of second elongate members including a second sleeve slidably supported thereon, each second elongate member being axially fixed;
  a plurality of linkage members, each linkage member having opposing first and second portions, the first portion operatively coupled to the corresponding first sleeve such that rotation of the corresponding first elongate member of the plurality of first elongate members moves the first portion in a first direction and the second portion in a second direction opposite of the first direction, each linkage member pivotally supported about a pivot disposed between the first and second portions that are axially aligned, the second portion operatively coupled to the second sleeve of a corresponding second elongate member of the plurality of second elongate members such that the first and second portions move along respective lengths of the corresponding first and second elongate members that are stationary relative to each other; and
  a plurality of drive members, each one of the plurality of drive members operatively coupled to the second portion of corresponding one of the plurality of linkage members; and
a surgical instrument detachably coupled to the instrument drive unit, the surgical instrument including:
  a plurality of driven members, each of the plurality of driven members operatively associated with corresponding one of the plurality of drive members of the instrument drive unit; and
  an end effector operatively coupled with the plurality of driven members, wherein translation of at least one of the plurality of driven members effects a first function of the end effector.

14. The robotic surgical assembly of claim 13, wherein rotation of the first elongate member pivots the corresponding one of the plurality of linkage members about the pivot.

15. The robotic surgical assembly of claim 14, wherein each first sleeve is threadably mounted on the corresponding first elongate member.

16. The robotic surgical assembly of claim 14, wherein the first sleeve has a first camming pin, and the first portion of the corresponding linkage member defines a first slot configured to slidably receive the first camming pin, whereby translation of the first sleeve along the first elongate member causes relative movement of the first camming pin within the first slot.

17. The robotic surgical assembly of claim 16, wherein each second elongate member of the plurality of second elongate members includes a second sleeve translatably mounted on the corresponding second elongate member, the second sleeve operatively associated with the second portion of the corresponding linkage member.

18. The robotic surgical assembly of claim 17, wherein the second sleeve has a second camming pin, and the second portion of the corresponding linkage member defines a second slot configured to slidably receive the second camming pin, whereby translation of the second sleeve causes relative movement of the first second pin within the second slot.

19. The robotic surgical assembly of claim 13, wherein each first elongate member of the plurality of first elongate members includes a pulley operatively coupled to the first actuator, wherein actuation of the first actuator causes rotation of the first elongate member.

20. The robotic surgical assembly of claim 13, wherein the surgical instrument further includes a plurality of cables, each cable having a first end coupled one of the plurality of the driven members of the surgical instrument and a second end operatively associated with the end effector.

21. The robotic surgical assembly of claim 13, wherein the instrument drive unit further includes a second actuator and a rotatable member coupled with the second actuator, and the surgical instrument further includes a gear member configured to operatively engage the rotatable member of the instrument drive unit, the gear member coupled with the end effector for concomitant rotation with the end effector.

22. The robotic surgical assembly of claim 21, wherein the first actuator of the instrument drive unit is controlled by telemanipulation.

23. The robotic surgical assembly of claim 21, wherein the first and second actuators are independently actuatable.

24. The robotic surgical assembly of claim 13, wherein the surgical instrument includes an elongate member extending distally from the driven assembly, the elongate member supporting the end effector at a distal end of the elongate member.

25. The robotic surgical assembly of claim 13, wherein the mount of the robotic arm is interposed between the instrument drive unit and the surgical instrument.

* * * * *